(12) United States Patent
Altmann-Jöhl et al.

(10) Patent No.: US 6,489,147 B1
(45) Date of Patent: Dec. 3, 2002

(54) GENE FOR ADENYLATE CYCLASE AND ITS USE

(75) Inventors: Regula Altmann-Jöhl, Weesen (CH); Peter Philippsen, Riehen (CH); Henning Althöfer, Limburgerhof (DE); Harald Seulberger, Neuhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,403

(22) PCT Filed: Dec. 29, 1997

(86) PCT No.: PCT/EP97/07309

§ 371 (c)(1), (2), (4) Date: Jun. 21, 1999

(87) PCT Pub. No.: WO98/29538

PCT Pub. Date: Jul. 9, 1998

(30) Foreign Application Priority Data

Dec. 31, 1996 (CH) .................................................. 16/97

(51) Int. Cl.[7] .......................... C12P 17/12; C12N 15/60

(52) U.S. Cl. ..................... 435/122; 435/232; 435/252.3; 435/254.1; 435/255.4; 435/255.5; 435/255.2

(58) Field of Search ................................. 435/69.1, 106, 435/122, 232, 252.5, 252.1, 252.3, 254.1, 255.4, 255.5, 255.2

(56) References Cited

PUBLICATIONS

Said, H.M., et al. (1994) Am. J. Physiol. 267(6, Pt. 1), G955–G959.*
Shavlovskii, G.M., et al. (1990) Chem. Abst. 113, 94574s.*
Kataoka et al., *Cell*, vol. 43, 493–505, Dec. 1985.

* cited by examiner

*Primary Examiner*—Charles L. Patterson, Jr.
(74) *Attorney, Agent, or Firm*—Keil & Weinkauf

(57) ABSTRACT

A gene which contains the nucleotide sequence shown in SEQ ID NO:1 from nucleotide 671 to nucleotide 6295 or a nucleotide sequence which can be obtained therefrom by substitution, insertion or deletion of up to 30%, preferably up to 10%, particularly preferably up to 20%, especially preferably up to 5%, of the nucleotides, and whose gene product has the enzymatic activity of an adenylate cyclase, and its use.

11 Claims, 3 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 6703 base pairs
      (B) TYPE: nucleic acid
      (C) STRANDEDNESS: double (D) TOPOLOGY: linear (xi) SEQUENCE DESCRIPTION: SEQ ID NO: 1:

```
GATCCGGCCA CGCATGTATT CCACTATGTA CGCTATATCG CGGCCTCGCC TCCGTGCGGG      60

CGCACCGCCT TACACCTCAA AGCCGTAGCC TTTCATGCAG TCCTTGTACT TTTGCACCAG     120

TTCCTGGCAC TTGACCGCAT CCACGCCGTT GAACAGCAGA CAGCTGTCTC TCGCTTCCTT     180

CTCGGGCTTG CACACACAGC ATGGCTTTGG CTTGTCGGTA CTACTACCTT GTGAAACACC     240

TGGCACAGAA GAGGATTCAG GCATGATTAA TGCTACAGTT CTTGGACGAT CTTCCACCAC     300

CGTCCGTTCC TTGAGCTTTT TTCACTTATA TAGCTCAACG CGCAAAAATG CTGACGAATA     360

CACATACAGC GCGCAGCAAC CGCTTAGTGG TTATTGGCTG CTGGTAGCAG CTGGACCCGA     420

GAGTCGGCAG TATCTTGGGC TTCGGCATTA GCGTAGTTCA GCGTAGGGCC ATGGGATTAT     480

TAATATCATA TCGTACGGCA AGCTTGTTTT AATAAGGAGC CTTCGGCATG GACACGGATT     540

GTCGTGAACC ACAGCCGCAA CGGGGCGAAG AGCTCTTCTA GCAGGTAAAA GAAGAGCACG     600

CGGGTCGTAC AGAACACGCT GAAGTCGTTC CAGAAGCTTA GCGGAGCGGA TTGCTGAGCA     660
```

| | | |
|---|---|---|
| GAATAATTCG ATG GAT AGA AAA GCG CAC AGA GCG GGC GAG CGC CGG GCT | | 709 |
| Met Asp Arg Lys Ala His Arg Ala Gly Glu Arg Arg Ala | | |
| 1 5 10 | | |
| GCA GGC AGG ACA GAT GGG CGC GGA GGT TGG GAA CGC GGC GCG GAC GGG | | 757 |
| Ala Gly Arg Thr Asp Gly Arg Gly Gly Trp Glu Arg Gly Ala Asp Gly | | |
| 15 20 25 | | |
| CTG GCG GCG GGG TCG CGG CGC GAC TCT GTC GAT GAC AGC TGG TCG AGC | | 805 |
| Leu Ala Ala Gly Ser Arg Arg Asp Ser Val Asp Asp Ser Trp Ser Ser | | |
| 30 35 40 45 | | |
| CTA TCG AGC AAC TCG CAG GAG GCG CCA TTG GAG CAC GAG GTG CGG AGC | | 853 |
| Leu Ser Ser Asn Ser Gln Glu Ala Pro Leu Glu His Glu Val Arg Ser | | |
| 50 55 60 | | |
| GGC GGA CGG ATT GTG GAG CCG GGC AGC GAC TTG CCG CCA CAT ATG AAG | | 901 |
| Gly Gly Arg Ile Val Glu Pro Gly Ser Asp Leu Pro Pro His Met Lys | | |
| 65 70 75 | | |
| CAC AGT CGC GGG TTG CAT CAC GCG AGC TTT GCG CGC GTG AGC CAG CAC | | 949 |
| His Ser Arg Gly Leu His His Ala Ser Phe Ala Arg Val Ser Gln His | | |
| 80 85 90 | | |
| CCG AGC TCG CCG CTG GCA AAG CAG CTG CGG CCT GTG CGT AAC GTG ACC | | 997 |
| Pro Ser Ser Pro Leu Ala Lys Gln Leu Arg Pro Val Arg Asn Val Thr | | |
| 95 100 105 | | |
| ATG CAG TCT GCC GCT GAG GAC GAC GAT GCG CGG GCC ACA GGC GCG CCT | | 1045 |
| Met Gln Ser Ala Ala Glu Asp Asp Asp Ala Arg Ala Thr Gly Ala Pro | | |
| 110 115 120 125 | | |
| CCG CCA ATA CGG CGC ATA CCA TCG CGC GCA GGC TCG TTT TTT AAG CGC | | 1093 |
| Pro Pro Ile Arg Arg Ile Pro Ser Arg Ala Gly Ser Phe Phe Lys Arg | | |
| 130 135 140 | | |
| CTG ACC GGC CGC AAG AGC TCC ATC AAT GGC TCG GAG ACT TCC GCG GCG | | 1141 |
| Leu Thr Gly Arg Lys Ser Ser Ile Asn Gly Ser Glu Thr Ser Ala Ala | | |
| 145 150 155 | | |
| GCT GAT GCG GAC GTC GCG GCG GCG CCG TCT TCG CTG CGG CGT AAG GTG | | 1189 |
| Ala Asp Ala Asp Val Ala Ala Ala Pro Ser Ser Leu Arg Arg Lys Val | | |
| 160 165 170 | | |
| AAC ACA TTC ATC CAT GGA AAT GAA GCC AGG CGA GAC AGT AAG GGC ACA | | 1237 |
| Asn Thr Phe Ile His Gly Asn Glu Ala Arg Arg Asp Ser Lys Gly Thr | | |
| 175 180 185 | | |
| ATA TCG ACG TCT TCA GCG GAC AGT AGG CGT GGG TCG ACG GCC AGC GGC | | 1285 |
| Ile Ser Thr Ser Ser Ala Asp Ser Arg Arg Gly Ser Thr Ala Ser Gly | | |
| 190 195 200 205 | | |
| GGG AGT GCG TCG ATA ATT CAG CTT CCT GAC GGA CAG AGG CTC TCG TTG | | 1333 |

-continued

```
Gly Ser Ala Ser Ile Ile Gln Leu Pro Asp Gly Gln Arg Leu Ser Leu
                210                 215                 220

CAG GAA TAC AAG CCT GTG TCG CCC ACT ACC ACT GCC CTT TCT AGC GCA    1381
Gln Glu Tyr Lys Pro Val Ser Pro Thr Thr Thr Ala Leu Ser Ser Ala
            225                 230                 235

TCG AGC GCT GCT GCC CAG CAA GGC GGT GAC AGG AGC ACT GGC TCT CCT    1429
Ser Ser Ala Ala Ala Gln Gln Gly Gly Asp Arg Ser Thr Gly Ser Pro
        240                 245                 250

GTG CAT GTG CCG TGG GAT AAT GCG GAG GCT TCC AAC GAG CAC GAG TCG    1477
Val His Val Pro Trp Asp Asn Ala Glu Ala Ser Asn Glu His Glu Ser
    255                 260                 265

GGC GTA AAC ACA ACA TTC TTT AAT TTA GAC ATG GAC CTG AAC AAC CTC    1525
Gly Val Asn Thr Thr Phe Phe Asn Leu Asp Met Asp Leu Asn Asn Leu
270                 275                 280                 285

TCT GAC ATA ACG AGT GCC TAT CAG CAA CAG ACT GAG ACC ACT ACG AAT    1573
Ser Asp Ile Thr Ser Ala Tyr Gln Gln Gln Thr Glu Thr Thr Thr Asn
                290                 295                 300

GCC AAT CTG GAG GTA AAT ATG GCA AAC GCC GGC AAG CCT GTT GTG CAC    1621
Ala Asn Leu Glu Val Asn Met Ala Asn Ala Gly Lys Pro Val Val His
            305                 310                 315

ATG CCG CGG CCA CAG AAG CTT CCT GCG AGG GAA GTT CGC CAT ACC AAG    1669
Met Pro Arg Pro Gln Lys Leu Pro Ala Arg Glu Val Arg His Thr Lys
        320                 325                 330

GGA GCT GCG CAG TGG ACG GCT CCG GAG TCA TGG GAT GTT GAT GAC CCC    1717
Gly Ala Ala Gln Trp Thr Ala Pro Glu Ser Trp Asp Val Asp Asp Pro
    335                 340                 345

GTT ATC AAG CCA TCG AAA CAA AAA CAG AAG TGC CAC AAT CCA GCC CAT    1765
Val Ile Lys Pro Ser Lys Gln Lys Gln Lys Cys His Asn Pro Ala His
350                 355                 360                 365

CGG CAC CAT CGG CAC CAC TAC AGT CCT CGT TCG GAT ATG ACC GGA ACG    1813
Arg His His Arg His His Tyr Ser Pro Arg Ser Asp Met Thr Gly Thr
                370                 375                 380

TCT GGC GAT AAC AAT CGC TTG TCC GCA GAT CCA AAC CGG TAT TCA AAT    1861
Ser Gly Asp Asn Asn Arg Leu Ser Ala Asp Pro Asn Arg Tyr Ser Asn
            385                 390                 395

CTG GAG GAC TCA CCC AAT CAT AGC CGT TTG ACA GCA GCC TTT TCT CGA    1909
Leu Glu Asp Ser Pro Asn His Ser Arg Leu Thr Ala Ala Phe Ser Arg
        400                 405                 410

TCT CCA ATC CAC AGG GAT ATG TCT CCG CTT AGT ATC ATG AGT TCT GAT    1957
Ser Pro Ile His Arg Asp Met Ser Pro Leu Ser Ile Met Ser Ser Asp
    415                 420                 425

AGC ATT GTA TCC AGT AAC TCA GAT TCC TGT AGC TTT TCC GTC GTG AGT    2005
Ser Ile Val Ser Ser Asn Ser Asp Ser Cys Ser Phe Ser Val Val Ser
430                 435                 440                 445

AAC CCG GAA GAC ACG CCA AAA GAC ATC ACA CAT CCA GAC AAT GCT TCC    2053
Asn Pro Glu Asp Thr Pro Lys Asp Ile Thr His Pro Asp Asn Ala Ser
                450                 455                 460

ACC TCT TCG ATC CAT GCA CAA GAA CTT GAA AAT AAT GAT ATT GAG GAT    2101
Thr Ser Ser Ile His Ala Gln Glu Leu Glu Asn Asn Asp Ile Glu Asp
            465                 470                 475

GAT AAA CTG CAG CAT CAT TTA GAG AAG TAC TAC AAT CAC TTT AGT GAT    2149
Asp Lys Leu Gln His His Leu Glu Lys Tyr Tyr Asn His Phe Ser Asp
        480                 485                 490

ATT GAC TAT CAC AAA AAA TAC ACG ATC CGT ATT TTT AAT ACG GAC GAT    2197
Ile Asp Tyr His Lys Lys Tyr Thr Ile Arg Ile Phe Asn Thr Asp Asp
    495                 500                 505

ACT TTT ACA ACG CTA TCA TGT AGG CCG GAG ACT ACT GTA AAG GAA ATG    2245
Thr Phe Thr Thr Leu Ser Cys Arg Pro Glu Thr Thr Val Lys Glu Met
510                 515                 520                 525
```

```
ATA CCC CAG ATA AAG CGG AAA TTT AAC GTG CCC CCA GGT AAC TAC CAG    2293
Ile Pro Gln Ile Lys Arg Lys Phe Asn Val Pro Pro Gly Asn Tyr Gln
            530                 535                 540

GTT TCC CTT AAA GTC GGT AAG TTG TCA AAG GTA TTG AGG CCA ACA GCG    2341
Val Ser Leu Lys Val Gly Lys Leu Ser Lys Val Leu Arg Pro Thr Ala
            545                 550                 555

AAG CCA ATC TTA ATT CAA ATA CGA CTC CTG TTA TTC AAT GGT TAT AAG    2389
Lys Pro Ile Leu Ile Gln Ile Arg Leu Leu Leu Phe Asn Gly Tyr Lys
            560                 565                 570

AAG ACA GAT CGT TTA AAC ATT ATG GGC ATA GAA GAC TTG AGT TTT GTC    2437
Lys Thr Asp Arg Leu Asn Ile Met Gly Ile Glu Asp Leu Ser Phe Val
            575                 580                 585

TTC AGT TTT GTC TTC CAC CCC GTT ATT ACA TCA CAG TTA ACA TAT GAA    2485
Phe Ser Phe Val Phe His Pro Val Ile Thr Ser Gln Leu Thr Tyr Glu
590                 595                 600                 605

CAA GAG CAA AGG CTC AGT AAA GGT GAG TTC GTT CAT GTT GAC CTG CGT    2533
Gln Glu Gln Arg Leu Ser Lys Gly Glu Phe Val His Val Asp Leu Arg
            610                 615                 620

AAC ATG GAC CTT ACG ATT CCG CCG ATT ATT TTT TAT CAA CAT ACG TCT    2581
Asn Met Asp Leu Thr Ile Pro Pro Ile Ile Phe Tyr Gln His Thr Ser
            625                 630                 635

GAC ATT GAG AGT CTC GAT GTA TCC AAT AAT GCC AAT ATA TTC CTG CCT    2629
Asp Ile Glu Ser Leu Asp Val Ser Asn Asn Ala Asn Ile Phe Leu Pro
            640                 645                 650

TTG GAT TTC ATC GAG AGT GTG ATT AAG CTT TCC AGT TTA CGA ATG GTC    2677
Leu Asp Phe Ile Glu Ser Val Ile Lys Leu Ser Ser Leu Arg Met Val
            655                 660                 665

AAT ATT AGA GCG TCC CGA TTT CCT TCA AAT ATC TGT GAG GCA ACA AAG    2725
Asn Ile Arg Ala Ser Arg Phe Pro Ser Asn Ile Cys Glu Ala Thr Lys
670                 675                 680                 685

CTG ATC ACC CTT GAT TTG GAA AGG AAC TTT ATT AAA AGG GTA CCG GAC    2773
Leu Ile Thr Leu Asp Leu Glu Arg Asn Phe Ile Lys Arg Val Pro Asp
            690                 695                 700

CAG ATG TCT AAG CTT ACA AAT TTA ACA ATT TTG AAT CTA AGG TGC AAT    2821
Gln Met Ser Lys Leu Thr Asn Leu Thr Ile Leu Asn Leu Arg Cys Asn
            705                 710                 715

GAA TTG GAC AGG CTA CCA AGG GGG TTT AAA GAC TTA AAA AGT CTT CAA    2869
Glu Leu Asp Arg Leu Pro Arg Gly Phe Lys Asp Leu Lys Ser Leu Gln
            720                 725                 730

CTA CTC GAT ATT TCT TCT AAT AAG TTT AAT ATC TAC CCC GAG GTT ATT    2917
Leu Leu Asp Ile Ser Ser Asn Lys Phe Asn Ile Tyr Pro Glu Val Ile
            735                 740                 745

AAT TCA TGT ACA AAC TTG CTG CAG CTA GAC TTG TCC TAT AAC AAG ATT    2965
Asn Ser Cys Thr Asn Leu Leu Gln Leu Asp Leu Ser Tyr Asn Lys Ile
750                 755                 760                 765

AGA TCC TTA CCG GAT AGT ATG AAT CAG CTG CAA AAA CTA GCC AAA ATT    3013
Arg Ser Leu Pro Asp Ser Met Asn Gln Leu Gln Lys Leu Ala Lys Ile
            770                 775                 780

AAC CTA TCG AAC AAC CGC ATA ACA CAT GTC AAT GAT CTT TCG AAA ATG    3061
Asn Leu Ser Asn Asn Arg Ile Thr His Val Asn Asp Leu Ser Lys Met
            785                 790                 795

ACT TCT CTG CGG ACC TTG GAC TTG AGA TAT AAT AGA ATT GAG TCT ATA    3109
Thr Ser Leu Arg Thr Leu Asp Leu Arg Tyr Asn Arg Ile Glu Ser Ile
            800                 805                 810

AAA TGT CGG GTA CCA AAC CTC CAG AAT CTT TTC CTG ACC GAA AAT AGA    3157
Lys Cys Arg Val Pro Asn Leu Gln Asn Leu Phe Leu Thr Glu Asn Arg
815                 820                 825

CTC ACA ATG TTT GAT GAT GAC CAG CTG ATG CTT AGA ACA CTA GAA TTG    3205
Leu Thr Met Phe Asp Asp Asp Gln Leu Met Leu Arg Thr Leu Glu Leu
830                 835                 840                 845
```

-continued

```
CAG AGA AAT CCA TTA TCG ATA CTC ACT TTG AAG AAC GAC TAC TTG GAA      3253
Gln Arg Asn Pro Leu Ser Ile Leu Thr Leu Lys Asn Asp Tyr Leu Glu
            850                 855                 860

CAT TTG ACA AGT TTA TCT ATA AGC AAA GCA AAG TTA GCG GTT TTA CCT      3301
His Leu Thr Ser Leu Ser Ile Ser Lys Ala Lys Leu Ala Val Leu Pro
            865                 870                 875

GAG AGC TTG CTA AGG CGG CTA CCA CGT TTA GAG AAA CTG GAA TTA AGT      3349
Glu Ser Leu Leu Arg Arg Leu Pro Arg Leu Glu Lys Leu Glu Leu Ser
            880                 885                 890

GAA AAT AGC TTG ACT GTT CTG CCT CCA GAT ATC AAG CAC CTG AAG AAG      3397
Glu Asn Ser Leu Thr Val Leu Pro Pro Asp Ile Lys His Leu Lys Lys
            895                 900                 905

TTA GTT CAT CTC TCA GTG GCC AAA AAT AAA CTG GAA TCA CTT CCA GAC      3445
Leu Val His Leu Ser Val Ala Lys Asn Lys Leu Glu Ser Leu Pro Asp
910                 915                 920                 925

GAA ATC GCT TCT CTA AAA AAC CTT AAG ATG CTT GAC TTA CAT TGT AAT      3493
Glu Ile Ala Ser Leu Lys Asn Leu Lys Met Leu Asp Leu His Cys Asn
            930                 935                 940

AAT TTG ATG ACA TTG CCT GCT GCT CTA TCA ACA CTC AGT TTG ACT TTT      3541
Asn Leu Met Thr Leu Pro Ala Ala Leu Ser Thr Leu Ser Leu Thr Phe
            945                 950                 955

GTG AAC ATT TCT TCA AAT ATG TTA TCT GGG CAT CAT GAA TTG TAT CGC      3589
Val Asn Ile Ser Ser Asn Met Leu Ser Gly His His Glu Leu Tyr Arg
            960                 965                 970

ACC TTC CAA GGA ACT TCA AAT ATT GCA AAA TCA TTG ATG TTT TTA AGC      3637
Thr Phe Gln Gly Thr Ser Asn Ile Ala Lys Ser Leu Met Phe Leu Ser
    975                 980                 985

GCT GCA GAC AAC CAG ATG GGT GAT AAA TTC TGG GAG ATA TTC AAT ACT      3685
Ala Ala Asp Asn Gln Met Gly Asp Lys Phe Trp Glu Ile Phe Asn Thr
990                 995                 1000                1005

TTT AAG ACG TTG AAA GTT TTA AAC CTG TCA TAT AAC AAC TTT ATG GCC      3733
Phe Lys Thr Leu Lys Val Leu Asn Leu Ser Tyr Asn Asn Phe Met Ala
            1010                1015                1020

CTG CCA GAA CTT GAG ATG GAG AAT TTA ACT GAA CTC TAC TTA TCG GGT      3781
Leu Pro Glu Leu Glu Met Glu Asn Leu Thr Glu Leu Tyr Leu Ser Gly
            1025                1030                1035

AAT CAT TTA ACA ACG CTC TCT GGT GAA GCT TTC TTA AAG CTC AAA TCA      3829
Asn His Leu Thr Thr Leu Ser Gly Glu Ala Phe Leu Lys Leu Lys Ser
            1040                1045                1050

CTT AGA GTT CTC ATG CTG AAT GCT AAT AAT TTG CAG TCC CTG CCA GCA      3877
Leu Arg Val Leu Met Leu Asn Ala Asn Asn Leu Gln Ser Leu Pro Ala
            1055                1060                1065

GAG ATC TCG CAA CTC TCG CAA CTC TCC GTC ATT GAT GTC GGT TCG AAT      3925
Glu Ile Ser Gln Leu Ser Gln Leu Ser Val Ile Asp Val Gly Ser Asn
1070                1075                1080                1085

CAG CTC AAG TAC AAT ATA TCC AAC TAC CAT TAT GAC TGG AAT TGG AGA      3973
Gln Leu Lys Tyr Asn Ile Ser Asn Tyr His Tyr Asp Trp Asn Trp Arg
            1090                1095                1100

CAG AAC ACC GAG CTA AAG TAC CTA AAC TTC TCC GGT AAC ACT AGA TTT      4021
Gln Asn Thr Glu Leu Lys Tyr Leu Asn Phe Ser Gly Asn Thr Arg Phe
            1105                1110                1115

GAA ATC AAA AGT GCT ATG GAG TAT GGA ACC AAT ATG CAT TTA TCT GAC      4069
Glu Ile Lys Ser Ala Met Glu Tyr Gly Thr Asn Met His Leu Ser Asp
            1120                1125                1130

CTT ACT GTC TTG AAA CAG CTC AGA GTT TTA GGC TTA ATG GAT GTG ACC      4117
Leu Thr Val Leu Lys Gln Leu Arg Val Leu Gly Leu Met Asp Val Thr
            1135                1140                1145

CTA AAC ACT TCG CGA GTC CCT GAT GAT GGG GTC AAC TTC AGA TTA AGA      4165
Leu Asn Thr Ser Arg Val Pro Asp Asp Gly Val Asn Phe Arg Leu Arg
```

-continued

```
1150                1155                1160                1165

ACA ATG GGT TCT ACA ATC AAT GGT ATG GAG TAT GGT GTA GCG GAC TCG    4213
Thr Met Gly Ser Thr Ile Asn Gly Met Glu Tyr Gly Val Ala Asp Ser
            1170                1175                1180

TTG GGG CAG ACA GAT TCT GTT TCA ACC AGA GAC GTC ACT TTT GAA CGT    4261
Leu Gly Gln Thr Asp Ser Val Ser Thr Arg Asp Val Thr Phe Glu Arg
            1185                1190                1195

TTC AGG GGA AAT GAA GAT GAG TGT CTG ATT TGT TTG TAT GAT GGA ATT    4309
Phe Arg Gly Asn Glu Asp Glu Cys Leu Ile Cys Leu Tyr Asp Gly Ile
            1200                1205                1210

AAC GAT AAT ACA AAC ACA GGC CAT AAA ATA TCA CAG GTC ATA AGA GAT    4357
Asn Asp Asn Thr Asn Thr Gly His Lys Ile Ser Gln Val Ile Arg Asp
            1215                1220                1225

ATA TAT GAT CGC ATA TTA GTG CGG TCT GTG GAG AAA TAT GGT GAC TCA    4405
Ile Tyr Asp Arg Ile Leu Val Arg Ser Val Glu Lys Tyr Gly Asp Ser
1230                1235                1240                1245

ACG CCA GCC GAA ATT CGC GAT GCC CTA CGC TTC AGT TTC CTG CAA CTA    4453
Thr Pro Ala Glu Ile Arg Asp Ala Leu Arg Phe Ser Phe Leu Gln Leu
            1250                1255                1260

AAC AAA GAA ATT AAT TCC TCG ATA CTT GCT GCT GGT AAT AAC AAG AAT    4501
Asn Lys Glu Ile Asn Ser Ser Ile Leu Ala Ala Gly Asn Asn Lys Asn
            1265                1270                1275

AGT AAC GGT AAC ACT AAT AAT AAT AAC ACT AAT AAT AAT AAT AAT        4549
Ser Asn Gly Asn Thr Asn Asn Asn Asn Thr Asn Asn Asn Asn Asn
            1280                1285                1290

AAT GGA AAT AAT AAT ACT AAT TCA AAT GGT GAA TCT GTC GTC TTA ACT    4597
Asn Gly Asn Asn Asn Thr Asn Ser Asn Gly Glu Ser Val Val Leu Thr
            1295                1300                1305

GCC GCC GAT TCA TTG AGT GGC GCG TCG GTC ACA GTT GTA TTC ATG AAG    4645
Ala Ala Asp Ser Leu Ser Gly Ala Ser Val Thr Val Val Phe Met Lys
1310                1315                1320                1325

GGC AAA AAT ATC TAT ACT GCC AAC ATC GGA AAC GCA ACG GCT ATT CTC    4693
Gly Lys Asn Ile Tyr Thr Ala Asn Ile Gly Asn Ala Thr Ala Ile Leu
            1330                1335                1340

TCT AAG GGC AAC GCT GAT TAT CGT ATT CTA ACA CGC AAA CAC GTT CCT    4741
Ser Lys Gly Asn Ala Asp Tyr Arg Ile Leu Thr Arg Lys His Val Pro
            1345                1350                1355

ACT GAT ACT GAA GAG TTT GAA AGA ATC CGA TTA TCC GGA GGA TAT GTC    4789
Thr Asp Thr Glu Glu Phe Glu Arg Ile Arg Leu Ser Gly Gly Tyr Val
            1360                1365                1370

GAC AAT AAG AGG GTG AAT GGA GTA TCC GAA ATA TCC AGA GCA ATA GGA    4837
Asp Asn Lys Arg Val Asn Gly Val Ser Glu Ile Ser Arg Ala Ile Gly
            1375                1380                1385

TTT TTT GAT CTC TTA CCA CAT ATT CAC GCC TCA CCT GAT ATT AGT GAG    4885
Phe Phe Asp Leu Leu Pro His Ile His Ala Ser Pro Asp Ile Ser Glu
1390                1395                1400                1405

ACC ACC TTA ACA TAT ACG GAC GAT ATG TTG GTA ATA GCG ACC CAG AGT    4933
Thr Thr Leu Thr Tyr Thr Asp Asp Met Leu Val Ile Ala Thr Gln Ser
            1410                1415                1420

TTA CTA TCT TAT GTC AGT CTG GAA AAA ATA TGC GAT ATT GCT AGG GAA    4981
Leu Leu Ser Tyr Val Ser Leu Glu Lys Ile Cys Asp Ile Ala Arg Glu
            1425                1430                1435

AAC AAG TCT CAA CCA ATG CTA GCA GCC GAA AGA ATG AAG GAT TAT GCG    5029
Asn Lys Ser Gln Pro Met Leu Ala Ala Glu Arg Met Lys Asp Tyr Ala
            1440                1445                1450

ATT GCA TAT GGA TGT ACG GAT AAT ATA ACC ATA CTG TGC GTT TCA TTT    5077
Ile Ala Tyr Gly Cys Thr Asp Asn Ile Thr Ile Leu Cys Val Ser Phe
            1455                1460                1465

AAT AAA AAT GTT GGC AAG CAG AAA CAA TTC TCT CTG AAC AAA AGC GAT    5125
```

```
                                                      -continued

Asn Lys Asn Val Gly Lys Gln Lys Gln Phe Ser Leu Asn Lys Ser Asp
1470                1475                1480                1485

CTA CTG GGT CGG CGT CTA AAC TTT GAA GAT GTT TCA CTG CGC AGA TTG        5173
Leu Leu Gly Arg Arg Leu Asn Phe Glu Asp Val Ser Leu Arg Arg Leu
                1490                1495                1500

CGC CCA GAA ATT GCC CCA CCA ACT GGA CAT CTG GCA ATC GTA TTC ACA        5221
Arg Pro Glu Ile Ala Pro Pro Thr Gly His Leu Ala Ile Val Phe Thr
            1505                1510                1515

GAT ATT AAA AAC TCA ACA TTC CTT TGG GAA CTA TTC CCC AAC GCA ATG        5269
Asp Ile Lys Asn Ser Thr Phe Leu Trp Glu Leu Phe Pro Asn Ala Met
        1520                1525                1530

CGT GTG GCA ATA AAA GCT CAT AAC GAC ATT ATG CGT AGA ACA CTT CGA        5317
Arg Val Ala Ile Lys Ala His Asn Asp Ile Met Arg Arg Thr Leu Arg
    1535                1540                1545

ATA TTT GGT GGA TAC GAA GTC AAG ACC GAA GGT GAT GCT TTT ATG GTT        5365
Ile Phe Gly Gly Tyr Glu Val Lys Thr Glu Gly Asp Ala Phe Met Val
1550                1555                1560                1565

GCT TTC CCA ACG CCT ACC AGT GCT CTG GTA TGG TGC TTA ACG ATT CAA        5413
Ala Phe Pro Thr Pro Thr Ser Ala Leu Val Trp Cys Leu Thr Ile Gln
                1570                1575                1580

CTT AAA CTA CTG GAG CTT GAT TGG CCA GAG GAG ATC ACA TCC ATC AAA        5461
Leu Lys Leu Leu Glu Leu Asp Trp Pro Glu Glu Ile Thr Ser Ile Lys
            1585                1590                1595

TCC GGC TGT ATG ATT ACA GAT GAC AGC GGA AAT ACA ATA TAC CAG GGT        5509
Ser Gly Cys Met Ile Thr Asp Asp Ser Gly Asn Thr Ile Tyr Gln Gly
        1600                1605                1610

CTC TCT GTT CGT ATG GGC ATC CAC TGG GGA TGT CCT GTG CCG GAG GTG        5557
Leu Ser Val Arg Met Gly Ile His Trp Gly Cys Pro Val Pro Glu Val
    1615                1620                1625

GAT ATA GTG ACG CAG AGA ATG GAT TAC CTT GGT CCT ATG GTC AAC AAG        5605
Asp Ile Val Thr Gln Arg Met Asp Tyr Leu Gly Pro Met Val Asn Lys
1630                1635                1640                1645

GCA GCT AGA GTG TCA GCA ACC GCT GAT GGT GGC CAG ATT ACA CTG AGC        5653
Ala Ala Arg Val Ser Ala Thr Ala Asp Gly Gly Gln Ile Thr Leu Ser
                1650                1655                1660

AGC GAC TTC CTA GCG GAA TTA AAC AAA ATA ATG AAA CTC CAC CAC ATG        5701
Ser Asp Phe Leu Ala Glu Leu Asn Lys Ile Met Lys Leu His His Met
            1665                1670                1675

GTC GTA CAG GAT AAA AAG CCA CTG AAG GAG GTG TAT GGT GAA GAA TTC        5749
Val Val Gln Asp Lys Lys Pro Leu Lys Glu Val Tyr Gly Glu Glu Phe
        1680                1685                1690

GTG GGC GAA GTT TTA GAG CGT GAG ATC CAA ATG TTA GAT AAC GTT GGA        5797
Val Gly Glu Val Leu Glu Arg Glu Ile Gln Met Leu Asp Asn Val Gly
    1695                1700                1705

TTG GTT CTG GAA GAA CTG GGG GAG CAG AAG TTA AAG GGT CTG GAA ACT        5845
Leu Val Leu Glu Glu Leu Gly Glu Gln Lys Leu Lys Gly Leu Glu Thr
1710                1715                1720                1725

CGG GAA TTC ATA ACT ATT GCG TAT CCC AAG CAA TTG GCA GCT AGA CAT        5893
Arg Glu Phe Ile Thr Ile Ala Tyr Pro Lys Gln Leu Ala Ala Arg His
                1730                1735                1740

ACC ATG TCC ACA GGG GAG AAA AGC ACC AAC ATT GTC AAC GAT AAA TAT        5941
Thr Met Ser Thr Gly Glu Lys Ser Thr Asn Ile Val Asn Asp Lys Tyr
            1745                1750                1755

GTT CTC CAA TTG AAA GTA ATT TCC ACA ACT TTG GAG AAT CTT CTT TCA        5989
Val Leu Gln Leu Lys Val Ile Ser Thr Thr Leu Glu Asn Leu Leu Ser
        1760                1765                1770

ACT GTT AAC GGC GGT CTG ATC GAA ATC GAC AAT AGT GTC CTA CAA CTA        6037
Thr Val Asn Gly Gly Leu Ile Glu Ile Asp Asn Ser Val Leu Gln Leu
    1775                1780                1785
```

```
CCC ACA CAT ATG ACT CGT GAT AAA AAG GTT GAT AAA GCG CTG AGC CAG      6085
Pro Thr His Met Thr Arg Asp Lys Lys Val Asp Lys Ala Leu Ser Gln
1790                1795                1800                1805

AAC ACG GAA TAC GAT TGG ATA TCC TTG TTG GAT CAT CTT GTC ACT AGG      6133
Asn Thr Glu Tyr Asp Trp Ile Ser Leu Leu Asp His Leu Val Thr Arg
                1810                1815                1820

CTG GAG TCT ACG GTA GCA ATG CTG CAG CTG CGG CAG CGA TTG GAG GGT      6181
Leu Glu Ser Thr Val Ala Met Leu Gln Leu Arg Gln Arg Leu Glu Gly
            1825                1830                1835

GGC TTG GAG ATC TGT CGA CCA GGT AAC AAT ACG AAA AAA TCA GTA TTC      6229
Gly Leu Glu Ile Cys Arg Pro Gly Asn Asn Thr Lys Lys Ser Val Phe
        1840                1845                1850

GAG CTG CTG GAT CTG CTG TGC ACT GGA ACA GGT TTC AAG CGA GAT ACG      6277
Glu Leu Leu Asp Leu Leu Cys Thr Gly Thr Gly Phe Lys Arg Asp Thr
    1855                1860                1865

CCG TCT GAA AAT AAA TAACTTAACA GTACATAATT GTCAGACTAT TTCGGAGTCC      6332
Pro Ser Glu Asn Lys
1870                187

TGCATCCGAA ATAACCAGCG TATGATATAT TACGTTATTA AAATGCTATT TACGAATGAT    6392

CAGTCTCACC GTGGCGCTAG AATGATCTCA AGCGTATTTA TAATGTAGGC TATTTCTGTG    6452

CCTCCAAGTC CTTCATCTCA AACTGCTGTC TGTTCTGAGA ACTGCCATGA TAGGGAGACT    6512

CAGCCCCACC CGTAATAGGT TCCTGATCTA TGAGACCCTC AAAAAACGTG TCGCGAAGCT    6572

CGCGCCACCT CGTGGTCCAC GTCCCCAAAA ACACCAAAAT CAAGCTCGAA CAGAGCTGCA    6632

GGAAAAACCA CGAGAACGAC GGAAGCTGCT TCGTGTGAAA CCACACCACT AGGAGATTTA    6692

TCGCATGGAT C                                                         6703

(2) INFORMATION FOR SEQ ID NO: 2:

(i) SEQUENCE CHARACTERISTICS:
        (A) LENGTH: 1874 amino acids
        (B) TYPE: amino acid
        (C) STRANDEDNESS: single
        (D) TOPOLOGY: linear (xi) SEQUENCE DESCRIPTION: SEQ ID NO: 2:

Met Asp Arg Lys Ala His Arg Ala Gly Glu Arg Arg Ala Ala Gly Arg
1               5                   10                  15

Thr Asp Gly Arg Gly Gly Trp Glu Arg Gly Ala Asp Gly Leu Ala Ala
            20                  25                  30

Gly Ser Arg Arg Asp Ser Val Asp Asp Ser Trp Ser Ser Leu Ser Ser
        35                  40                  45

Asn Ser Gln Glu Ala Pro Leu Glu His Glu Val Arg Ser Gly Gly Arg
    50                  55                  60

Ile Val Glu Pro Gly Ser Asp Leu Pro Pro His Met Lys His Ser Arg
65                  70                  75                  80

Gly Leu His His Ala Ser Phe Ala Arg Val Ser Gln His Pro Ser Ser
                85                  90                  95

Pro Leu Ala Lys Gln Leu Arg Pro Val Arg Asn Val Thr Met Gln Ser
            100                 105                 110

Ala Ala Glu Asp Asp Ala Arg Ala Thr Gly Ala Pro Pro Pro Ile
        115                 120                 125

Arg Arg Ile Pro Ser Arg Ala Gly Ser Phe Phe Lys Arg Leu Thr Gly
    130                 135                 140

Arg Lys Ser Ser Ile Asn Gly Ser Glu Thr Ser Ala Ala Ala Asp Ala
145                 150                 155                 160
```

-continued

```
Asp Val Ala Ala Pro Ser Ser Leu Arg Arg Lys Val Asn Thr Phe
            165                 170                 175

Ile His Gly Asn Glu Ala Arg Arg Asp Ser Lys Gly Thr Ile Ser Thr
            180                 185                 190

Ser Ser Ala Asp Ser Arg Arg Gly Ser Thr Ala Ser Gly Gly Ser Ala
            195                 200                 205

Ser Ile Ile Gln Leu Pro Asp Gly Gln Arg Leu Ser Leu Gln Glu Tyr
    210                 215                 220

Lys Pro Val Ser Pro Thr Thr Ala Leu Ser Ser Ala Ser Ser Ala
225                 230                 235                 240

Ala Ala Gln Gln Gly Gly Asp Arg Ser Thr Gly Ser Pro Val His Val
            245                 250                 255

Pro Trp Asp Asn Ala Glu Ala Ser Asn Glu His Glu Ser Gly Val Asn
            260                 265                 270

Thr Thr Phe Phe Asn Leu Asp Met Asp Leu Asn Asn Leu Ser Asp Ile
        275                 280                 285

Thr Ser Ala Tyr Gln Gln Gln Thr Glu Thr Thr Thr Asn Ala Asn Leu
    290                 295                 300

Glu Val Asn Met Ala Asn Ala Gly Lys Pro Val Val His Met Pro Arg
305                 310                 315                 320

Pro Gln Lys Leu Pro Ala Arg Glu Val Arg His Thr Lys Gly Ala Ala
            325                 330                 335

Gln Trp Thr Ala Pro Glu Ser Trp Asp Val Asp Asp Pro Val Ile Lys
            340                 345                 350

Pro Ser Lys Gln Lys Gln Lys Cys His Asn Pro Ala His Arg His His
            355                 360                 365

Arg His His Tyr Ser Pro Arg Ser Asp Met Thr Gly Thr Ser Gly Asp
    370                 375                 380

Asn Asn Arg Leu Ser Ala Asp Pro Asn Arg Tyr Ser Asn Leu Glu Asp
385                 390                 395                 400

Ser Pro Asn His Ser Arg Leu Thr Ala Ala Phe Ser Arg Ser Pro Ile
            405                 410                 415

His Arg Asp Met Ser Pro Leu Ser Ile Met Ser Ser Asp Ser Ile Val
            420                 425                 430

Ser Ser Asn Ser Asp Ser Cys Ser Phe Ser Val Val Ser Asn Pro Glu
        435                 440                 445

Asp Thr Pro Lys Asp Ile Thr His Pro Asp Asn Ala Ser Thr Ser Ser
    450                 455                 460

Ile His Ala Gln Glu Leu Glu Asn Asn Asp Ile Glu Asp Asp Lys Leu
465                 470                 475                 480

Gln His His Leu Glu Lys Tyr Tyr Asn His Phe Ser Asp Ile Asp Tyr
            485                 490                 495

His Lys Lys Tyr Thr Ile Arg Ile Phe Asn Thr Asp Asp Thr Phe Thr
            500                 505                 510

Thr Leu Ser Cys Arg Pro Glu Thr Thr Val Lys Glu Met Ile Pro Gln
        515                 520                 525

Ile Lys Arg Lys Phe Asn Val Pro Pro Gly Asn Tyr Gln Val Ser Leu
    530                 535                 540

Lys Val Gly Lys Leu Ser Lys Val Leu Arg Pro Thr Ala Lys Pro Ile
545                 550                 555                 560

Leu Ile Gln Ile Arg Leu Leu Phe Asn Gly Tyr Lys Lys Thr Asp
            565                 570                 575

Arg Leu Asn Ile Met Gly Ile Glu Asp Leu Ser Phe Val Phe Ser Phe
```

-continued

```
                580             585             590
Val Phe His Pro Val Ile Thr Ser Gln Leu Thr Tyr Glu Gln Glu Gln
                595             600             605

Arg Leu Ser Lys Gly Glu Phe Val His Val Asp Leu Arg Asn Met Asp
610             615             620

Leu Thr Ile Pro Pro Ile Ile Phe Tyr Gln His Thr Ser Asp Ile Glu
625             630             635             640

Ser Leu Asp Val Ser Asn Asn Ala Asn Ile Phe Leu Pro Leu Asp Phe
                645             650             655

Ile Glu Ser Val Ile Lys Leu Ser Ser Leu Arg Met Val Asn Ile Arg
                660             665             670

Ala Ser Arg Phe Pro Ser Asn Ile Cys Glu Ala Thr Lys Leu Ile Thr
                675             680             685

Leu Asp Leu Glu Arg Asn Phe Ile Lys Arg Val Pro Asp Gln Met Ser
690             695             700

Lys Leu Thr Asn Leu Thr Ile Leu Asn Leu Arg Cys Asn Glu Leu Asp
705             710             715             720

Arg Leu Pro Arg Gly Phe Lys Asp Leu Lys Ser Leu Gln Leu Leu Asp
                725             730             735

Ile Ser Ser Asn Lys Phe Asn Ile Tyr Pro Glu Val Ile Asn Ser Cys
                740             745             750

Thr Asn Leu Leu Gln Leu Asp Leu Ser Tyr Asn Lys Ile Arg Ser Leu
                755             760             765

Pro Asp Ser Met Asn Gln Leu Gln Lys Leu Ala Lys Ile Asn Leu Ser
                770             775             780

Asn Asn Arg Ile Thr His Val Asn Asp Leu Ser Lys Met Thr Ser Leu
785             790             795             800

Arg Thr Leu Asp Leu Arg Tyr Asn Arg Ile Glu Ser Ile Lys Cys Arg
                805             810             815

Val Pro Asn Leu Gln Asn Leu Phe Leu Thr Glu Asn Arg Leu Thr Met
                820             825             830

Phe Asp Asp Gln Leu Met Leu Arg Thr Leu Glu Leu Gln Arg Asn
                835             840             845

Pro Leu Ser Ile Leu Thr Leu Lys Asn Asp Tyr Leu Glu His Leu Thr
                850             855             860

Ser Leu Ser Ile Ser Lys Ala Lys Leu Ala Val Leu Pro Glu Ser Leu
865             870             875             880

Leu Arg Arg Leu Pro Arg Leu Glu Lys Leu Glu Leu Ser Glu Asn Ser
                885             890             895

Leu Thr Val Leu Pro Pro Asp Ile Lys His Leu Lys Lys Leu Val His
                900             905             910

Leu Ser Val Ala Lys Asn Lys Leu Glu Ser Leu Pro Asp Glu Ile Ala
                915             920             925

Ser Leu Lys Asn Leu Lys Met Leu Asp Leu His Cys Asn Asn Leu Met
                930             935             940

Thr Leu Pro Ala Ala Leu Ser Thr Leu Ser Leu Thr Phe Val Asn Ile
945             950             955             960

Ser Ser Asn Met Leu Ser Gly His His Glu Leu Tyr Arg Thr Phe Gln
                965             970             975

Gly Thr Ser Asn Ile Ala Lys Ser Leu Met Phe Leu Ser Ala Ala Asp
                980             985             990

Asn Gln Met Gly Asp Lys Phe Trp Glu Ile Phe Asn Thr Phe Lys Thr
                995             1000            1005
```

-continued

```
Leu Lys Val Leu Asn Leu Ser Tyr Asn Asn Phe Met Ala Leu Pro Glu
        1010                1015                1020
Leu Glu Met Glu Asn Leu Thr Glu Leu Tyr Leu Ser Gly Asn His Leu
1025                1030                1035                1040
Thr Thr Leu Ser Gly Glu Ala Phe Leu Lys Leu Lys Ser Leu Arg Val
                1045                1050                1055
Leu Met Leu Asn Ala Asn Asn Leu Gln Ser Leu Pro Ala Glu Ile Ser
                1060                1065                1070
Gln Leu Ser Gln Leu Ser Val Ile Asp Val Gly Ser Asn Gln Leu Lys
        1075                1080                1085
Tyr Asn Ile Ser Asn Tyr His Tyr Asp Trp Asn Trp Arg Gln Asn Thr
        1090                1095                1100
Glu Leu Lys Tyr Leu Asn Phe Ser Gly Asn Thr Arg Phe Glu Ile Lys
1105                1110                1115                1120
Ser Ala Met Glu Tyr Gly Thr Asn Met His Leu Ser Asp Leu Thr Val
                1125                1130                1135
Leu Lys Gln Leu Arg Val Leu Gly Leu Met Asp Val Thr Leu Asn Thr
                1140                1145                1150
Ser Arg Val Pro Asp Asp Gly Val Asn Phe Arg Leu Arg Thr Met Gly
        1155                1160                1165
Ser Thr Ile Asn Gly Met Glu Tyr Gly Val Ala Asp Ser Leu Gly Gln
        1170                1175                1180
Thr Asp Ser Val Ser Thr Arg Asp Val Thr Phe Glu Arg Phe Arg Gly
1185                1190                1195                1200
Asn Glu Asp Glu Cys Leu Ile Cys Leu Tyr Asp Gly Ile Asn Asp Asn
                1205                1210                1215
Thr Asn Thr Gly His Lys Ile Ser Gln Val Ile Arg Asp Ile Tyr Asp
                1220                1225                1230
Arg Ile Leu Val Arg Ser Val Glu Lys Tyr Gly Asp Ser Thr Pro Ala
        1235                1240                1245
Glu Ile Arg Asp Ala Leu Arg Phe Ser Phe Leu Gln Leu Asn Lys Glu
        1250                1255                1260
Ile Asn Ser Ser Ile Leu Ala Ala Gly Asn Asn Lys Asn Ser Asn Gly
1265                1270                1275                1280
Asn Thr Asn Asn Asn Asn Asn Thr Asn Asn Asn Asn Asn Asn Gly Asn
                1285                1290                1295
Asn Asn Thr Asn Ser Asn Gly Glu Ser Val Val Leu Thr Ala Ala Asp
                1300                1305                1310
Ser Leu Ser Gly Ala Ser Val Thr Val Phe Met Lys Gly Lys Asn
        1315                1320                1325
Ile Tyr Thr Ala Asn Ile Gly Asn Ala Thr Ala Ile Leu Ser Lys Gly
        1330                1335                1340
Asn Ala Asp Tyr Arg Ile Leu Thr Arg Lys His Val Pro Thr Asp Thr
1345                1350                1355                1360
Glu Glu Phe Glu Arg Ile Arg Leu Ser Gly Gly Tyr Val Asp Asn Lys
                1365                1370                1375
Arg Val Asn Gly Val Ser Glu Ile Ser Arg Ala Ile Gly Phe Phe Asp
                1380                1385                1390
Leu Leu Pro His Ile His Ala Ser Pro Asp Ile Ser Glu Thr Thr Leu
        1395                1400                1405
Thr Tyr Thr Asp Asp Met Leu Val Ile Ala Thr Gln Ser Leu Leu Ser
        1410                1415                1420
```

-continued

```
Tyr Val Ser Leu Glu Lys Ile Cys Asp Ile Ala Arg Glu Asn Lys Ser
1425                1430                1435                1440

Gln Pro Met Leu Ala Ala Glu Arg Met Lys Asp Tyr Ala Ile Ala Tyr
            1445                1450                1455

Gly Cys Thr Asp Asn Ile Thr Ile Leu Cys Val Ser Phe Asn Lys Asn
            1460                1465                1470

Val Gly Lys Gln Lys Gln Phe Ser Leu Asn Lys Ser Asp Leu Leu Gly
        1475                1480                1485

Arg Arg Leu Asn Phe Glu Asp Val Ser Leu Arg Arg Leu Arg Pro Glu
        1490                1495                1500

Ile Ala Pro Pro Thr Gly His Leu Ala Ile Val Phe Thr Asp Ile Lys
1505                1510                1515                1520

Asn Ser Thr Phe Leu Trp Glu Leu Phe Pro Asn Ala Met Arg Val Ala
            1525                1530                1535

Ile Lys Ala His Asn Asp Ile Met Arg Arg Thr Leu Arg Ile Phe Gly
            1540                1545                1550

Gly Tyr Glu Val Lys Thr Glu Gly Asp Ala Phe Met Val Ala Phe Pro
            1555                1560                1565

Thr Pro Thr Ser Ala Leu Val Trp Cys Leu Thr Ile Gln Leu Lys Leu
       1570                1575                1580

Leu Glu Leu Asp Trp Pro Glu Ile Thr Ser Ile Lys Ser Gly Cys
1585                1590                1595                1600

Met Ile Thr Asp Asp Ser Gly Asn Thr Ile Tyr Gln Gly Leu Ser Val
            1605                1610                1615

Arg Met Gly Ile His Trp Gly Cys Pro Val Pro Glu Val Asp Ile Val
            1620                1625                1630

Thr Gln Arg Met Asp Tyr Leu Gly Pro Met Val Asn Lys Ala Ala Arg
            1635                1640                1645

Val Ser Ala Thr Ala Asp Gly Gly Gln Ile Thr Leu Ser Ser Asp Phe
       1650                1655                1660

Leu Ala Glu Leu Asn Lys Ile Met Lys Leu His His Met Val Val Gln
1665                1670                1675                1680

Asp Lys Lys Pro Leu Lys Glu Val Tyr Gly Glu Glu Phe Val Gly Glu
            1685                1690                1695

Val Leu Glu Arg Glu Ile Gln Met Leu Asp Asn Val Gly Leu Val Leu
        1700                1705                1710

Glu Glu Leu Gly Glu Gln Lys Leu Lys Gly Leu Glu Thr Arg Glu Phe
       1715                1720                1725

Ile Thr Ile Ala Tyr Pro Lys Gln Leu Ala Ala Arg His Thr Met Ser
1730                1735                1740

Thr Gly Glu Lys Ser Thr Asn Ile Val Asn Asp Lys Tyr Val Leu Gln
1745                1750                1755                1760

Leu Lys Val Ile Ser Thr Thr Leu Glu Asn Leu Leu Ser Thr Val Asn
            1765                1770                1775

Gly Gly Leu Ile Glu Ile Asp Asn Ser Val Leu Gln Leu Pro Thr His
            1780                1785                1790

Met Thr Arg Asp Lys Lys Val Asp Lys Ala Leu Ser Gln Asn Thr Glu
        1795                1800                1805

Tyr Asp Trp Ile Ser Leu Leu Asp His Leu Val Thr Arg Leu Glu Ser
        1810                1815                1820

Thr Val Ala Met Leu Gln Leu Arg Gln Arg Leu Glu Gly Gly Leu Glu
1825                1830                1835                1840

Ile Cys Arg Pro Gly Asn Asn Thr Lys Lys Ser Val Phe Glu Leu Leu
```

-continued

```
                         1845                  1850                    1855
Asp Leu Leu Cys Thr Gly Thr Gly Phe Lys Arg Asp Thr Pro Ser Glu
               1860                  1865                   1870
Asn Lys
```

GENE FOR ADENYLATE CYCLASE AND ITS USE

The present invention relates to the change in activity of the cell cAMP signal transduction pathway, which leads to a change in the central cell metabolism and is thus exploited for increasing the production rates for fine chemicals in fermentative processes.

The enzyme adenylate cyclase catalyzes the production of cAMP from ATP and, with the aid of cAMP, governs, in eukaryotes, signal transduction by the enzyme protein kinase A. cAMP binds to the regulatory subunit of protein kinase A, which leads to protein kinase A being activated (Taylor et al., 1990, Annual Rev Biochem: 971–1005). This kinase alters the activity of target proteins by esterifying the hydroxyl groups of specific serines of these proteins with a phosphate group. Protein kinase A is involved in a large number of cellular regulatory processes. On the one hand, the kinase modulates the activity of some transcription factors such as, for example, CREB (Brindle and Montminy, 1992, Curr Opin Genet & Dev, 2, 199–204), which leads to the synthetic rates of metabolic enzymes being altered. Moreover, the product of adenylate cyclase (cAMP) takes part in regulating the central cell metabolism by governing both synthesis and activity of enzymes of glycolysis, gluconeogenesis and the glyoxylate pathway. Thus, cAMP inhibits the synthesis of key enzymes of gluconeogenesis and of the glyoxylate pathway, such as fructose bisphosphatase, phosphoenolpyruvate carboxykinase and isocitrate lyase (Boy-Marcotte et al., 1996, Microbiology, 142:459–467). On the other hand, the activity of enzymes of glycolysis, such as phosphofructokinase, is increased by cAMP-mediated protein kinase A activity (Keβler and Eschrich, 1996, FEBS Lett., 395: 225–227). In addition, the cAMP-activated protein kinase A inactivates the formation of carbohydrate stores in yeasts and stimulates the degradation of carbohydrate stores in fungi (Pall and Robertson, 1988, Biochem Biophys Res Commun, 150: 365–370; Toda et al., 1985, Cell, 40: 27–36). The signal cascade, which is initiated by adenylate cyclase activity, thus plays a crucial role in regulating the substance fluxes in the cell. In particular, cAMP signal transduction alters the direction of the substance fluxes in the central metabolism so that the cAMP signal transduction chain plays a decisive role in providing substrates for synthesizing secondary metabolic products. Specific secondary metabolic products are commercially important fine chemicals. These include, for example, vitamins, carotinoids, amino acids, fragrances and antibiotics.

Fine chemicals have a wide range of industrial uses in animal and human nutrition, in the cosmetics industry and in medicine. In addition, carotinoids act as natural colorants. Fine chemicals are produced industrially by chemical synthesis or, increasingly, by fermentation.

Activation of adenylate cyclase in yeasts and fungi is governed by the RAS G proteins. RAS G proteins here act, for example, as sensors for the glucose concentration in the medium (Field et al., 1990, Science, 247: 464–467). Glucose in the medium leads to RAS being activated by exchanging the bound GDP for GTP. This process is made possible by an RAS-specific exchange factor. The RAS which is activated by GTP binding binds to, and activates, adenylate cyclase, which, in turn, forms cAMP. The signal pathway is switched off by the cAMP-specific phosphodiesterase, which converts cAMP into AMP (Ishikawa et al., 1988, Methods Enzymol., 159, 27–42). Adenylate cyclase is thus a central switchpoint for adaptation to changes in the nutritional environment of cells. In higher eukaryotes, adenylate cyclase is regulated by heterotrimeric G proteins (Federmann et al., 1992, Nature, 356: 159–161).

In prokaryotes, too, adenylate cyclase is involved in the regulation of metabolic processes. Here, cAMP regulates the expression of some catabolic operons by binding to a transcription factor (CRP) (Tagami et al., 1995 Mol Microbiol, 17, 251–258).

To optimize fermentative processes for the production of fine chemicals, the substance flux toward the desired product must be increased.

This can be effected in different ways:

Switching-off of negative regulatory mechanisms of metabolic pathways which lead to the product Inactivation of enzymes which compete with the enzymes of the metabolic pathways leading to the desired product Increase, in the cell, of the quantity or activity of enzymes of the metabolic pathways which lead to the product Since cellular processes proceed in a coordinated fashion owing to higher regulatory mechanisms, such regulatory mechanisms are targets for altering the substance fluxes in the cell.

It is therefore an object to alter regulatory mechanisms in cells in such a way that they allow an increased substance flux toward the desired product.

We have found that this object is achieved according to the invention by altering the activity of the cAMP-dependent signal transduction pathway, which constitutes a central regulator of a large number of metabolic pathways in the cell, so that the substance fluxes can be directed toward the desired product. There is a multiplicity of possibilities of manipulating microorganisms in such a way that they carry an altered activity of the cAMP-dependent signal transduction pathway. However, an altered activity of the cAMP signal transduction pathway for increasing the production of fine chemicals in microorganisms has not been described as yet.

One possibility of increasing the production rates of fine chemicals in microorganisms by altering the activity of the cAMP signal transduction pathway consists in increasing or lowering, in the cell, the enzyme activity of adenylate cyclase, depending on the synthesis to be carried out.

An increase in the quantity of enzyme, and thus an increase in enzyme activity, can be achieved by introducing the gene which encodes adenylate cyclase into the microorganism to be altered at a higher repetition frequency, or by eliminating factors which repress enzyme synthesis. Alternatively, it is possible to exchange the sequences which govern adenylate cyclase expression for sequences which allow increased gene expression. In addition, an increase in enzyme activity can be achieved, for example, by mutating the enzyme to increase substrate conversion, or by disrupting the effect of enzyme inhibitors.

Alternatively, cAMP or a chemical cAMP derivative may be added to the medium, which also leads to protein kinase A being activated.

To reduce the enzyme activity of adenylate cyclase in the cell, the encoding gene can be disrupted, or the activity of adenylate cyclase synthesis activators can be reduced. Adenylate cyclase mutations, which have a reduced activity, can also be applied. Such mutations can be achieved either by traditional methods such as, for example, by UV irradiation or mutagenic chemicals, or directed by means of genetic engineering methods such as deletions, insertions or substitutions.

Not only can the gene activity of adenylate cyclase be altered, it is also possible in the same way to alter the enzyme activity of phosphodiesterase of protein kinase A (catalytic and regulatory domain) and of the RAS proteins (including proteins which have an effect on RAS activity) as described above.

It is preferred to alter the enzyme activity of adenylate cyclase. To reduce the enzyme activity, the adenylate cyclase gene is disrupted. To disrupt the adenylate cyclase gene, a selection marker is inserted into the DNA sequence which encodes adenylate cyclase. Then, this DNA construct is transformed into the cell, where it disrupts the adenylate cyclase gene locus by means of homologous recombination. Thus, the cell is incapable of synthesizing functional adenylate cyclase and thus cAMP.

The invention relates to a gene which contains the nucleotide sequence shown in SEQ ID NO:1 from nucleotide 671 to nucleotide 6295 or a nucleotide sequence which can be obtained therefrom by substitution, insertion or deletion of up to 30%, preferably up to 20%, particularly preferably up to 10%, especially preferably up to 5%, of the nucleotides and, whose gene product has the enzymatic activity of an adenylate cyclase.

The invention furthermore relates to the use of one or more of the abovementioned nucleic acid sequences for constructing, by genetic engineering, microorganisms which compared with the starting organism are capable of increased fine chemical production. A starting organism is to be understood as meaning, in the following text, those microorganisms which are capable of producing the desired fine chemicals, but which carry no genetic alteration with regard to the nucleic acid sequences according to the invention.

The invention is preferably applied to the production of riboflavin.

The preferred nucleic acid sequence used is the adenylate cyclase gene. The adenylate cyclase gene is preferably isolated from the microorganism which synthesizes the fine chemical in question. The preferred microorganisms which are employed in the process according to the invention are fungi and yeasts.

However, it is also possible to use other microorganisms, for example bacteria. Microorganisms which are especially suitable for the production of riboflavin are bacteria of the genus Bacillus and coryneform bacteria of the genus Corynebacteria or Brevibacteria, and yeasts of the genus Candida and Saccharomyces and fungi of the genus Ashbya and Eremothecium. Very particularly suitable for the production of riboflavin are *Bacillus subtilis, Corynebacterium ammoniagenes, Candida flareri, Candida famata* and *Ashbya gossypii*.

The adenylate cyclase gene can be isolated by sequencing a plasmid gene library, by homologous or heterologous complementation of a mutant which carries a defect in the adenylate cyclase gene, or else by heterologous probing or PCR with heterologous primers. For subcloning purposes, the insert of the complementing plasmid can subsequently be minimized in size by suitable cleavage with restriction enzymes. After sequencing and identification of the putative gene, it is fused to the DNA sequence of the selection marker by molecular biology techniques. The plasmid, which carries the sequence of the adenylate cyclase gene, is cleaved in the adenylate cyclase gene, and the selection marker is cloned into this cleavage site. The adenylate cyclase DNA, which frames the selection marker DNA, is subsequently introduced into the cell.

Isolation and sequencing of plasmids from a genomic plasmid library of *Ashbya gossypii* gives an adenylate cyclase gene which has nucleotide sequences shown in SEQ. ID NO:1 and which, from nucleotide 671 to nucleotide 6295, encode the amino acid sequence given in SEQ ID NO:2 or its allelic variations. Allelic variations encompass, in particular, derivatives which are obtainable from the sequence shown in SEQ.ID NO:1 by means of deletion, insertion or substitution of up to 30%, preferably up to 20%, particularly preferably up to 10%, especially preferably up to 5%, of the nucleotides.

Arranged upstream of the adenylate cyclase genes is, in particular, a promoter of the nucleotide sequence of nucleotide 1–670 as shown in SEQ.ID NO:1 or a sequence which acts essentially the same. Thus, for example, a promoter may be arranged upstream of the gene which differs from the promoter of the abovementioned nucleotide sequence by one or more nucleotide exchanges, by an insertion or insertions, and/or a deletion or deletions, but without the functionality or efficacy of the promoter being adversely affected. Moreover, the promoter may be altered with regard to its efficacy, due to its sequence being altered, or it may be exchanged completely by other promoters.

One or more DNA sequences can be arranged upstream and/or downstream of the adenylate cyclase gene with or without a promoter arranged upstream, or with or without a terminator sequence, so that the gene is retained in its gene structure.

Preference is given to increasing the production of the fine chemical riboflavin (vitamin B2) by altering the cAMP signal transduction pathway. However, other fermentative processes for the production of other fine chemicals are to be optimized by such an alteration. Riboflavin is produced in fungi, yeasts or bacteria, preferably in the fungus *Ashbya gossypii*.

If the adenylate cyclase gene in riboflavin-producing microorganism strains of Ashbya gossypii is disrupted, it emerges, surprisingly, that incubation on a glucose-containing medium leads to an increased riboflavin formation. This is seen, inter alia, on culture plates by the visual appearance of the cultures, which show a deep yellow coloration caused by riboflavin, which is weakened by adding cAMP to the medium.

EXAMPLES

Example 1

Establishing a Genomic Gene Library of *Ashbya gossypii*

To establish a genomic DNA library of *Ashbya gossypii*, chromosomal DNA was isolated by the method of Wright and Philippsen (1991, Gene 109: 99–105) and Mohr (1995, PhD thesis, Center for Biological Studies, Basle University, Switzerland).

The genomic DNA was partially digested with Sau3A and fractioned in a sucrose density gradient. The largest fragments were ligated with vector pRS416 cleaved with Bam HI (Sikorski and Hieter, 1988, Genetics, 122; 19–27). The *E.coli* laboratory strain XL-1 blue was transformed with this ligation batch, and the resulting clones were employed for identifying the adenylate cyclase gene.

Example 2

Selection of the Adenylate Cyclase Gene-encoding Fragment

Figure 1:
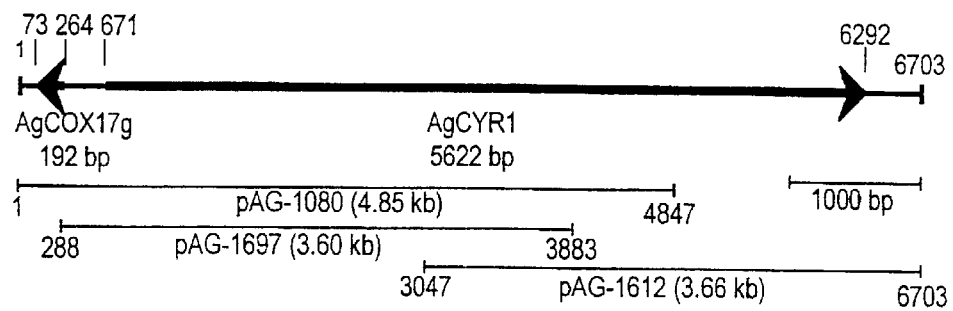
FIG. 1 describes the adenylate cyclase gene locus of *Ashbya gossypii* and identifies the subsequences covered by vectors pAG 1080, 1697 and 1612. Vector pAG 1080 and vector pAG1612 thus comprise the total sequence of the adenylate cyclase gene locus (encoding sequence nucleotide 671–6295).

Plasmids were purified from some clones described in Example 1, and the DNA of the inserts was sequenced. A computer-aided homology search based on the GCG program of Wisconsin University allowed DNA sequences to be identified which show homology to the *Saccharomyces cerevisiae* and *Saccharomyces kluyveri* adenylate cyclases. Plasmid pAG1080 (insert shown in FIG. 1), for example, contained a large portion of the adenylate cyclase gene and was sequenced. Screening of further plasmid libraries with a hybridizing probe complementary to plasmid pAG1080 led to the identification of plasmids pAG1687 and pAG1612, which, together with plasmid pAG1080, contain all of the DNA of the *Ashbya gossypii* adenylate cyclase gene (FIG. 1). The sequence is shown in SEQ. ID NO: 1. The portion which encodes adenylate cyclase starts at nucleotide 671 and ends at nucleotide 6295. At the nucleotide level, this encoding nucleic acid sequence from *Ashbya gossypii* shows an identity with *Saccharomyces kluyveri* adenylate cyclase of 66%. The amino acid sequence of the *Ashbya gossypii* adenylate cyclase, which was derived from the encoding region, shows an identity with the *Klyveromyces lactis* adenylate cyclase amino acid sequence of 63.5%.

Example 3

Generation of the Construct for Disrupting the Adenylate Cyclase Gene in *Ashbya gossypii*

Figure 2:
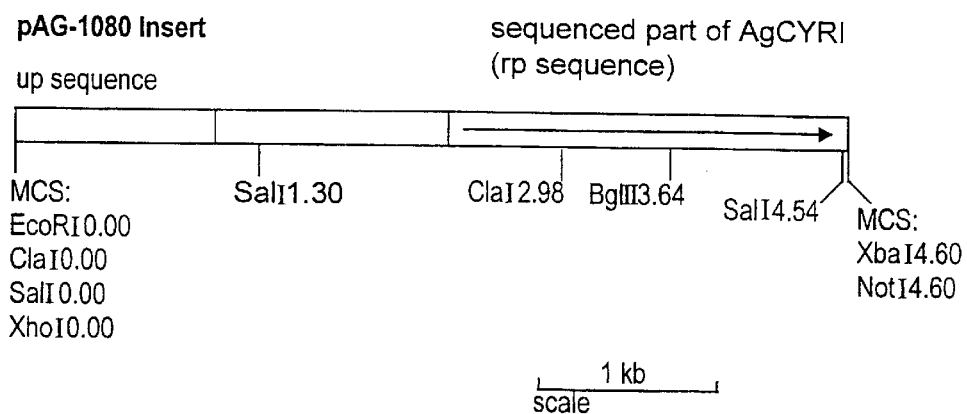
FIG. 2 shows cleavage sites for important restriction enzymes in the adenylate cyclase gene fragment of plasmid pAG 1080. The Bgl II clevage site, which is also described in Example 3, is also shown.
Figure 3:
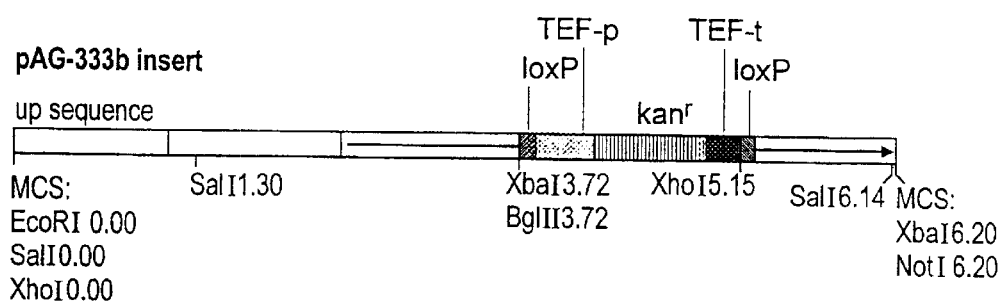
FIG. 3 shows the NotI-EcoRI fragment of vector pAG-333b. This fragment can be employed for disrupting the adenylate cyclase gene locus.

The resulting adenylate cyclase gene fragment in vector pAG 1080 was cleaved with Bgl II (FIG. 2). The resulting ends were then filled up with Klenow polymerase, treated with phosphatase and ligated to the 1.6 kb EcoRV-PvuII DNA fragment of pUG6 (Güldener et al., 1996, Nucleic Acids Research, 24: 2519–2524). The adenylate cyclase fragment of pAG 1080 now contains the DNA sequence of the Kanamycin resistance gene and the sequence of the promoter and terminator of the TEF gene (Wach et al., 1994, Yeast, 10: 1793–1808) flanked by loxP sequences from plasmid pUG6. From this vector construct, the NotI-EcoRI fragment, which, inter alia, contains the adenylate cyclase subsequence, was cloned into vector pBSII-SK which had been cleaved with NotI and EcoRI (termed vector pAG-333b hereinbelow, FIG. 3).

Example 5

Transformation of the Adenylate Cyclase Gene Disruption Construct into *Ashbya gossypii*

The 6.2 kb NotI-EcoRI fragment was cleaved out of pAG-333b, purified and transformed into the fungus wild-type *Ashbya gossypii* strain by electroporation of freshly germinated spores. The wild-type strain is to be understood as meaning ATCC strain 10895. The transformants can be selected by adding the amino glycoside G418 (200 μg/ml) to the growth medium (1% casein peptone, 1% yeast extract, 2% glucose and 0.1% myo-inositol). The transformants were then clonally purified by micromanipulation (Steiner and Philipsen, 1995, Genetics, 140: 973–987) and examined for the disruption of the adenylate cyclase gene by Southern analysis. For example, a strain was found (AGΔ1-T333b) which showed the desired disruption in the adenylate cyclase gene.

Example 6

Effect of the Adenylate Cyclase Gene Disruption on the Riboflavin Formation of *Ashbya gossypii*

A surprising indication of the effect of the cAMP quantities on riboflavin production was obtained in strain AGΔ1-T333b. In this adenylate cyclase disruptant of the fungus *Ashbya gossypii*, riboflavin concentrations of 36 mg/l are achieved. However, the addition of 1 mM cAMP to the medium (see Example 5) already leads to a drop in riboflavin concentration to 23 mg/l. To determine these values, a liquid culture of the selected transformants (Example 5) can be centrifuged and the $OD_{445}$ of the supernatant can be determined ($\epsilon$(riboflavin)=12500 liter $mol^{-1}$ $cm^1$).

When observing the visual appearance of strain AGΔ1-T333b when grown on solid medium (see medium of Example 5 with added agar), the addition of cAMP to the medium leads to a decrease in yellow coloration—and thus in riboflavin formation—of the *Ashbya gossypii* colonies. Also, when compared with the wild-type strain, strain AGΔ1-T333b, when grown on solid medium, shows an increased yellow coloration.

These experiments demonstrate the effect of cAMP on riboflavin production under the chosen experimental conditions.

We claim:

1. A process for the production of riboflavin, which process comprises growing a microorganism which has been subjected to genetic alteration in the gene encoding adenylate cyclase.

2. The process of claim 1, wherein the gene encoding adenylate cyclase which is homologous for the microorganism in question.

3. The process of claim 1, wherein the microorganism is a bacterium.

4. The process of claim 1, wherein the microorganism is a bacterium of the genus Bacillus or Corynebacterium.

5. The process of claim 1, wherein the microorganism is a eukaryotic microorganism.

6. The process of claim 1, wherein the microorganism is a filamentous fungus.

7. The process of claim 1, wherein the microorganism is a filamentous fungus of the genus Ashbya or Eremothecium.

8. The process of claim 1, wherein the microorganism is *Ashbya gossypli.*

9. The process of claim 1, wherein the microorganism is a yeast.

10. The process of claim 1, wherein the microorganism is a yeast of the genus Candida, Pichia or Saccharomyces.

11. A process for constructing, by genetic engineering, microorganisms which compared with the starting organism are capable of increased production of riboflavin (vitamin B2), comprising the step of transforming said microorganisms with the gene encoding adenylate cyclase.

* * * * *